United States Patent [19]
Reed

[11] Patent Number: 4,470,573
[45] Date of Patent: Sep. 11, 1984

[54] DEVICE FOR SHAPING COLOR TEST SAMPLES OF DENTAL CROWN PORCELAIN

[76] Inventor: Terry L. Reed, P.O. Box 103, Barboursville, W. Va. 25504

[21] Appl. No.: 489,374

[22] Filed: Apr. 28, 1983

[51] Int. Cl.³ .............................. B29C 1/14; B29C 1/06
[52] U.S. Cl. ................................... 249/66 R; 249/124; 249/142; 249/151; 425/441
[58] Field of Search ............... 425/441; 249/122, 124, 249/135, 142, 151, 66 R, 54, 163, 164

[56] References Cited
U.S. PATENT DOCUMENTS
1,000,187 8/1911 Moore .

FOREIGN PATENT DOCUMENTS
56-164832 12/1981 Japan ................................ 425/441

OTHER PUBLICATIONS
Prior art as shown in FIG. 1 and 1a of the drawing [Reed appln. Ser. No. 489,374].

Primary Examiner—Willard E. Hoag
Attorney, Agent, or Firm—Wood, Herron & Evans

[57] ABSTRACT

A device for shaping color test samples of porcelain formulations for use in making dental crowns, comprising a mandrel having a axial bore, a cylindrical rod insertable axially into the bore of the mandrel, and a releasable coupling element between the rod and the mandrel which permits rotation of the rod relative to the mandrel but resists axial movement between the two. At one end the mandrel has a cut-out section which exposes an end portion of the cylindrical rod in the axial bore. This section forms a radially curved molding surface on which a porcelain test sample can be formed having a curvature approximating that of a dental crown. The adherent sample is released from the rod at the molding surface by twisting the rod in the bore, without moving the rod axially. The color of a fired sample molded in this cut-out section has been found to better approximate the color of an actual crown of the same composition, then does the color of a flat sample formed with prior-art sample forming devices, from the same composition.

8 Claims, 7 Drawing Figures

DEVICE FOR SHAPING COLOR TEST SAMPLES OF DENTAL CROWN PORCELAIN

FIELD OF THE INVENTION

This invention relates to apparatus used in dentistry, and more particularly to a device for making color test samples of porcelain mixtures used in the making of dental crowns.

BACKGROUND OF THE INVENTION

Because of subtle chemical differences, age, and a variety of other factors, the teeth of patients in need of dental crowns vary in color to a significant degree. Porcelain is commonly used in the manufacture of dental crowns, and in order to properly match the color of a dental crown with the tooth color of a given patient, many porcelain formulations are currently available from which the dentist or orthodontist may choose. These porcelain formulations are supplied by their manufacturers in the form of white powders and are mixed with water to make a paste which is then molded to crown shape and fired. While color tabs are available to show the color of a formulation supplied under a given identification number, the actual color will usually vary slightly but noticeably from batch to batch. It is therefore the better practice to make a test color sample for each batch, and fire it; this insures a more precise determination of the color of a crown made using that porcelain batch. This procedure allows the dentist to choose or mix a porcelain formulation of the appropriate shade for a particular patient before the crown is actually made.

One prior art device for making such test samples or "tabs" is shown in FIG. 1, where it is labeled as prior art. That device consists of upper and lower rectangular plates which are pinned at one end to permit lateral sliding movement relative to one another. The upper plate includes a U-shaped cut out at its free end, the end being beveled so that its thickness diminishes toward the edge of the cut-out. In forming a color test sample or tab with that device, a porcelain formulation in the form of a moldable paste in packed in the cut out so that it generally conforms to the edgewise shape of the cut out. The paste is quite sticky, and tends to cling to the lower plate. It is dislodged without breaking by sliding the upper plate laterally across the lower plate until the plates are separated. The test tab (shown in FIG. 1a) can be carefully removed by pressing it transversely from the U-shaped cut out, and can then be fired.

A difficulty with that device is that the color of the porcelain test sample thereby formed does not match the color of an actual crown made from the same formulation, as closely as is desirable. Under inspection by a trained ceramist, a color difference is frequently apparent between a porcelain test sample as heretofore made, and a crown made from the same formulation.

An important aspect of this invention is the determination that a test sample or tab having curved and tapered surfaces approximating the configuration of a crown will provide a better indication of the true color of the crown formed from a given porcelain formulation, than will a flat tab. However, prior to this invention, it has proved difficult to make such a curved test sample or tab. The compacted, unfired porcelain tab formed in a curved mold is strongly adherent to the mold and has not easily been removed without crumbling.

SUMMARY OF THE INVENTION

It is among the primary objects of this invention to provide a device for making test samples or tabs of porcelain formulations, whereby the tabs have a configuration approximating the tapered shape and transverse and longitudinal curvature of a dental crown, so that after firing, the tab closely approximates the perceived color of a dental crown formed from the same porcelain formulation.

The device of this invention for making a curved test sample comprises a mandrel formed with an axial bore, a rod adapted to be inserted lengthwise into the axial bore, and an o-ring or other coupling means which mounts the rod within the mandrel so as to permit rotation of the rod within the mandrel bore while resisting axial movement therebetween. The mandrel is formed with a milled-out or cut-away section at one end, extending from the mandrel's outer surface and curving inwardly, preferably less than half the thickness of the bore, thereby intersecting the bore and exposing one rounded side of the rod therein. The exposed surface of the rod provides a convex mold surface, and the adjacent walls of the mandrel form outer tapered edges. Porcelain of a given test formulation is packed on these exposed surfaces and shaped to the curvature of the mandrel, to form a test sample having a concave, arcuate inner surface and a convex outer surface, with tapered edges between them. This shape approximates the configuration of a dental crown.

To avoid crumbling of the shaped paste when removed from the molding surface, the test sample is disengaged and removed from the mandrel and rod in a two step operation. First, the rod is rotated within the mandrel, but without moving it axially. This releases the test sample from the convex surface of the rod. Next, the mandrel is lightly tapped to release the edges of the sample from the tapered edge surfaces formed by the exposed mandrel walls in the cut-out. At his point, the adherence of the sample to the rod has been released. The rod can be withdrawn axially, if necessary, but this is usually unnecessary. The tab is then ready for firing and subsequent evaluation of its color.

DETAILED DESCRIPTION OF THE INVENTION

Figure 5:
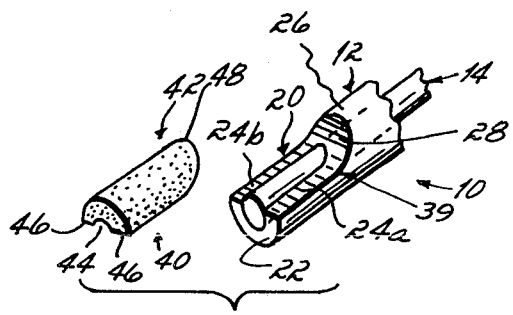
FIG. 5 is a view of the sample, and the sample forming end of the device of FIG. 2, after separation of the sample from the device.

Referring now to the drawings, the device 10 of this invention comprises a hollow cylindrical mandrel 12 and an elongated rod 14 which is received axially in the mandrel. The mandrel 12 has an axial through bore 16 forming an annulus or wall 18. A cut-out section 20 is formed at one end of mandrel 12 and extends to and intersects axial bore 16. As best shown in FIG. 5, the cut-out section 20 extends longitudinally from an end 22 of the mandrel 12 at a constant radial depth to form opposed edge surfaces 24a and 24b in the wall 18, and then gradually curves or tapers to the outer surface 26 of mandrel 12, thereby forming a tapered end surface 28. As viewed in FIG. 3, the plane of surfaces 24a, b lies above the axis of bore 16 but is low enough that the cut out intersects the bore. Although edge surfaces 24a, b are shown as being generally flat in the drawings, they may be tapered outwardly from the axial bore 16. Rod 14 is sized to fit closely but movably within the axial bore 16 of mandrel 12, and has an enlarged end or gripping section 31 which is of the same outside diameter as mandrel 12. The end section 31 provides a means for grasping the rod to rotate it relative to the mandrel.

Figures 2, 3:
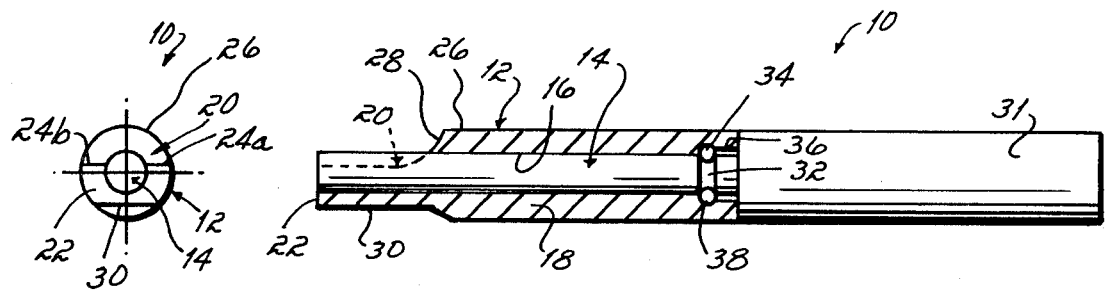
FIG. 2 is a side view in partial cross section of a preferred form of the device for making porcelain test samples, in accordance with this invention.
FIG. 3 is an end view of the device shown in FIG. 2.

An annular groove 32 is cut in rod 14 forward of end section 31, and receives an o-ring 34 (see FIG. 2). O-ring 34 acts as a coupling for axially positioning rod 14 in mandrel 12. In order to receive the rod 14 within axial bore 16 with the o-ring 34 seated in the groove 32, a counter-bore 36 is formed in mandrel bore 16 at the end thereof which is opposite cut-out section 20. Counter-bore 36 is of larger diameter and concentric to axial bore 16, and leads to a groove 38 which is in axial alignment with the rod groove 32 when the rod is fully inserted in bore 16. The radial dimension of the o-ring 34 when seated in groove 32 is slightly greater than the diameter of bore 36 so that when rod 14 is slid into counter-bore 36, o-ring 34 is compressed. This compression is relieved when o-ring 34 seats between the two grooves 32 and 38. The radial dimension of o-ring 34 is such that the ring is compressed even when seated in the opposed grooves 32 and 38, so that rotation of rod 14 within bore 16 is frictionally resisted and inadvertent axial movement or disengagement of the rod 14 from the mandrel 12 is strongly resisted. If desired, rod 14 may be separated from mandrel 12 for cleaning or for replacement of the o-ring 34 by forcibly pulling rod 14 axially from the mandrel 12.

Figure 4:
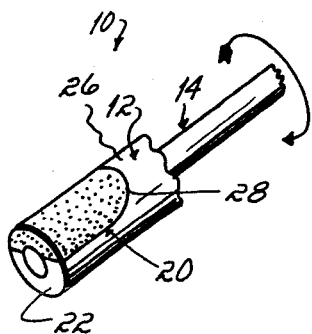
FIG. 4 is a partial isometric view of the sample forming end of the device of FIG. 2, in which a molded tab is shown prior to release from the device, and showing the axial rotation of the rod by which the adherence is broken.
Figure 6:
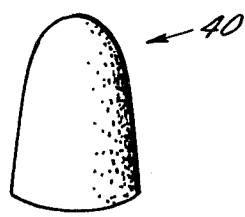
FIG. 6 is a view of a finished dental crown.

When mandrel 12 and rod 14 are assembled as shown in FIG. 2, a portion of the convex surface of rod 14 near the end thereof is exposed within the cut-out section 20 of mandrel 12. As shown in FIGS. 4 and 5, the exposed surface of rod 14, in combination with the opposed edge surfaces 24a, b and the tapered end surface 28 formed in the mandrel wall 18 by cut out section 20, together form a molding surface 39 which approximates the curvature of a dental crown 40 (see FIG. 6).

A flat 30 is cut in the wall 18 of mandrel 12 opposite cut-out section 20. This optional flat 30 provides a convenient thumb or finger rest as will be described.

A test sample 42 of a given porcelain mixture is formed with the apparatus 10 of this invention in the following manner. The porcelain mixture in paste form is packed into the molding surface 39, as with a spatula, covering the rod 14 and the edge surfaces 24a, b and tapered end surface 28 of the mandrel 12. The outer surface of the mix is formed to the same diameter as mandrel 12. The porcelain paste inwardly thus conforms to the shape of molding surface 39, to form a sample 42 having a concave center portion 44, tapered edges 46, a tapered end 48 and a thickness equal to the radial dimension from the molding surface 39 to the outer surface 26 of mandrel 12.

Figure 1:
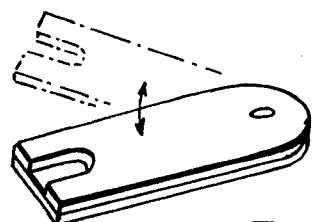
FIG. 1 is an isometric view, labeled "Prior Art", showing an existing device for forming flat color test samples of dental crown porcelains.
Figure 1A:
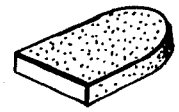
FIG. 1a labeled "Prior Art", is an isometric view of a flat test sample formed by the prior art device of FIG. 1.

As already noted, it has proven difficult to remove a curved sample from a mold, without crumbling. Porcelain mixtures in paste form have only green strength, but are adherent to mold surfaces. Therefore prior art molds such as described above have been configured to produce a test sample which is flat on the bottom and top, i.e. as viewed in a plane transverse to its longitudinal dimension (see FIG. 1a).

This adhesion problem is solved by the apparatus 10 of this invention in the following manner. While the rod 14 and mandrel 12 are held from axial movement by o-ring 34, the o-ring 34 permits the rod 14 to be rotated within axial bore 16 of mandrel 12. In order to separate the sample 42 from the convex surface of the rod 14 within cut-out section 20, rod 14 is gently rotated relative to the mandrel 12. This separates the sample 42 from the rod 14 without breaking or crumbling the shaped porcelain. Once separated from the convex surface of rod 14, the sample 42 may be removed from the edge surfaces 24a, b and tapered end surface 28 of the mandrel wall 18 by lightly tapping the mandrel 12. The surfaces should be polished or buffed, to facilitate release.

In accordance with this invention, a test sample 42 is formed which more nearly approximates the curvature of a finished dental crown so that after firing the sample 42 will provide a more accurate indication of what the color of a dental crown will be for that particular formulation of porcelain.

While the invention has been described in connection with a certain presently preferred embodiment, it will be apparent to those skilled in the art that modifications thereof can be used in the practice of the invention without departing from the principle of this invention.

What is claimed is:

1. A device for forming a test sample of a porcelain formulation so as to have a curvature and taper approximating those of a dental crown, in order to demonstrate the color of a crown made from such formulation, said device comprising:
   a mandrel formed with a bore;
   a rod adapted to be slid lengthwise into said bore and fitting closely therein;
   coupling means for retaining said rod in the bore of said mandrel and permitting rod rotation but restricting axial movement of the rod;
   said mandrel being formed with a cut-out section intersecting said bore so as to expose a portion of said rod therein, the surface of said mandrel in said cut-out section and the exposed surface portion of said rod together defining a molding surface for configuring said porcelain formulation to form a test sample having a curvature and taper approximating those of a dental crown.

2. A device as in claim 1 in which said molding surface defines a test sample shape comprising a concave central portion disposed between spaced, tapered edge sections, and a tapered end portion.

3. A device as in claim 1 in which said coupling means is an o-ring encircling said rod and engagable between opposed annular grooves formed around said rod and in said bore, the engagement of said o-ring in said grooves permitting rotation of said rod relative to said mandrel but resisting axial movement thereof.

4. A device as in claim 3 in which said mandrel is formed with an enlarged counterbore in said bore leading to the groove therein, the groove of said mandrel being aligned with the groove of said rod when said rod is inserted in said bore, and wherein said o-ring is compressed between said groove, said compression permitting rotation of said rod relative to said mandrel while resisting axial movement thereof.

5. A device as in claim 1 in which the cut-away section of said mandrel adjacent to said exposed portion of said rod presents opposed edge surfaces and a tapered end surface.

6. A device as in claim 5 in which said cut-out section of said mandrel does not extend to the axis of said bore.

7. A device for shaping a test sample of a porcelain formulation to a curvature approximating that of a dental crown, in order to determine the color of a crown made from said porcelain formulation, said device comprising:

a cylindrical mandrel having an axial bore within an annular wall, the bore extending through the mandrel from end to end thereof;

a rod adapted to be inserted longitudinally into said axial bore;

a releasable coupling adapted to connect said rod to said mandrel so as to permit rotation of said rod therewithin while resisting axial disengagement of said rod from said mandrel;

said mandrel being formed with a cut-out section intersecting said axial bore so as to expose a portion of said rod in said bore, the exposed portion of the rod and the wall of said mandrel adjacent said exposed portion forming a molding surface, said molding surface being adapted to receive said porcelain formulation and form said test sample in a curvature approximating that of said dental crown, said rod being rotatable within said axial bore to detach said test sample therefrom without damaging said test sample whereupon said test sample may be removed from said molding surface.

8. A device as in claim 7 wherein said molding surface is at an end of said mandrel.

* * * * *